United States Patent
Doyle et al.

(10) Patent No.: US 11,957,314 B2
(45) Date of Patent: Apr. 16, 2024

(54) SURGICAL VISUALIZATION AND MEDICAL IMAGING DEVICES AND METHODS USING NEAR INFRARED FLUORESCENT POLYMERS

(71) Applicant: University of Rochester, Rochester, NY (US)

(72) Inventors: Paula Jaye Doyle, Rochester, NY (US); Jay Evan Reeder, Syracuse, NY (US); Ronald Wesley Wood, Rochester, NY (US)

(73) Assignee: University of Rochester, Rochester, NY (US)

( * ) Notice: Subject to any disclaimer, the term of this patent is extended or adjusted under 35 U.S.C. 154(b) by 1079 days.

(21) Appl. No.: 16/485,976

(22) PCT Filed: Feb. 16, 2018

(86) PCT No.: PCT/US2018/018526
§ 371 (c)(1),
(2) Date: Aug. 14, 2019

(87) PCT Pub. No.: WO2018/152427
PCT Pub. Date: Aug. 23, 2018

(65) Prior Publication Data
US 2020/0229890 A1    Jul. 23, 2020

Related U.S. Application Data

(60) Provisional application No. 62/460,802, filed on Feb. 18, 2017.

(51) Int. Cl.
| | | |
|---|---|---|
| *A61B 1/04* | (2006.01) | |
| *A61B 5/00* | (2006.01) | |
| *A61B 5/107* | (2006.01) | |
| *A61B 17/42* | (2006.01) | |
| *A61B 34/30* | (2016.01) | |
| *A61B 90/30* | (2016.01) | |
| *A61K 49/00* | (2006.01) | |
| *A61B 1/06* | (2006.01) | |
| *A61B 17/00* | (2006.01) | |
| *A61B 90/00* | (2016.01) | |

(52) U.S. Cl.
CPC ............ *A61B 1/043* (2013.01); *A61B 5/0071* (2013.01); *A61B 5/0086* (2013.01); *A61B 5/1076* (2013.01); *A61B 17/4241* (2013.01); *A61B 34/30* (2016.02); *A61B 90/30* (2016.02); *A61K 49/0034* (2013.01); *A61B 1/06* (2013.01); *A61B 2017/00818* (2013.01); *A61B 2017/00831* (2013.01); *A61B 2090/062* (2016.02); *A61B 2090/304* (2016.02); *A61B 90/37* (2016.02); *A61B 2090/373* (2016.02)

(58) Field of Classification Search
CPC .. A61K 49/0034; A61B 1/043; A61B 5/1076; A61B 5/1071; A61B 5/0086; A61B 90/30; A61B 1/267; A61B 17/4241; A61B 34/30; A61B 2090/062; A61B 2090/304; A61B 2090/373; A61B 90/37; A61B 2017/00818; A61B 2017/00831
See application file for complete search history.

(56) References Cited

U.S. PATENT DOCUMENTS

| | | | | |
|---|---|---|---|---|
| 2005/0043716 A1* | 2/2005 | Frimer | ................... | A61F 2/0063 606/1 |
| 2011/0017217 A1* | 1/2011 | Wood | .................... | A61M 16/04 128/207.14 |
| 2014/0030349 A1 | 10/2014 | Mather et al. | | |
| 2014/0356293 A1* | 12/2014 | Reeder | ................... | A61K 47/46 424/9.6 |
| 2015/0087969 A1 | 3/2015 | Shekhar et al. | | |

FOREIGN PATENT DOCUMENTS

| | | |
|---|---|---|
| CN | 102188229 | 9/2011 |
| CN | 103249359 | 8/2013 |
| EP | 2641531 A1 | 9/2013 |

OTHER PUBLICATIONS

Torbati et al., J. Biomed. Mat. Research B: Applied Biomat., 2014, 102B, p. 1236-1243. (Year: 2014).*
Stevenson et al., Biomaterials, 2015, 54, p. 168-176. (Year: 2015).*
Ashbaugh et al., PNAS, 2016, p. E6919-E6928. (Year: 2016).*
(Continued)

*Primary Examiner* — Michael G. Hartley
*Assistant Examiner* — Leah H Schlientz
(74) *Attorney, Agent, or Firm* — David L. Nocilly; Bond, Schoeneck & King PLLC

(57) ABSTRACT

A surgical visualization and medical imaging device and related computer based imaging methods and systems are disclosed. The surgical devices of the present invention use indocyanine green dye combined with a plastic, and are used in enhanced surgical imaging in applications such as robotically assisted surgeries. A near infrared light source, such as an 805 nm laser, may be used to excite the surgical device so that the device emits 835 nm light. Both the excitation and emission wavelengths penetrate tissue and blood, and provide enhanced imaging of surgical procedures. The resulting fluorescence image allows a user to readily determine relative tissue depth, to identify tissue inhomogeneity, to detect masses or tissue irregularities, to pinpoint anatomical holes, and to visualize tears.

16 Claims, 10 Drawing Sheets

(56) References Cited

OTHER PUBLICATIONS

Kimmig et al., Journal of Surgical Oncology, 2016, 113, p. 554-559). (Year: 2016).*
International Search Report and Written Opion Form PCT/ISA/210 and ISA/237, International Application No. PCT/US2018/018526, pp. 1-14, International Filing Date Feb. 16, 2018, dated May 18, 2018.
CN Office Action, App. No. 201880026010.9, dated Apr. 30, 2021, pp. 1-11.

* cited by examiner

SECTION A-A

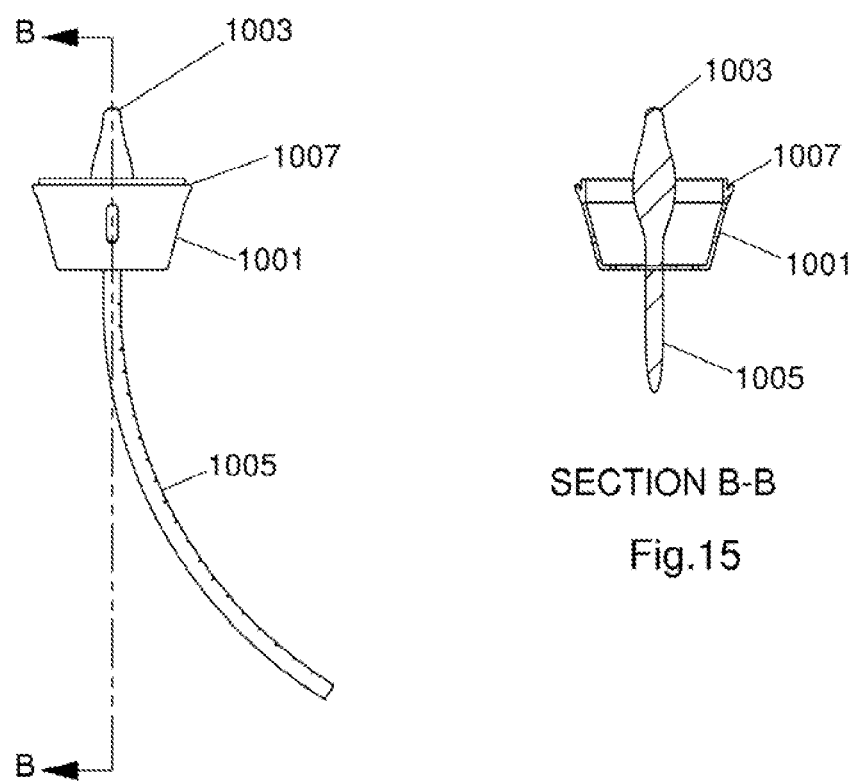

SURGICAL VISUALIZATION AND MEDICAL IMAGING DEVICES AND METHODS USING NEAR INFRARED FLUORESCENT POLYMERS

CROSS-REFERENCE TO RELATED APPLICATIONS

This is a National Stage Application, filed under 35 U.S.C. 371, of International Patent Application No. PCT/US2018/018526, filed on Feb. 16, 2018, which claims priority to U.S. Provisional Application 62/460,802, filed Feb. 18, 2017, the entire contents of each of which are incorporated herein by reference in their entirety.

BACKGROUND OF THE INVENTION

1. Field of the Invention

This invention relates generally to medical imaging and, more specifically, to devices and methods using near infrared fluorescent polymers for enhanced imaging of surgical procedures.

2. Description of the Related Art

Various surgical techniques require the use of surgical assist devices such as manipulators, sizers, backers, and the like. These surgical assist devices help with the identification of anatomical structures and operative tissues by physically moving, stretching, and relocating tissue at the surgical site. For example, surgical assist devices provide form and structure to tissue and related surgical targets to facilitate various surgical procedures, and allow the surgeon to move and reshape operative cutting planes. Examples of such surgical assist devices include, for example, vaginal manipulators, bowel sizers, uterine manipulators, and the like.

With the growing use of robotically assisted surgeries, surgical assist devices may be also be used to help with visualization of the surgical area, provide form and structure to tissue and related surgical targets, and enable better manipulation of the surgical area. While robotically assisted surgeries allow for less invasive and more complex surgical procedures than was possible with traditional surgical approaches, the surgeon may not be able to visualize the target site fully and to discern important aspects about the surgical site, such as the depth and quality of the tissue and the presence and quality of different types of tissue, particularly since robotic surgeries are performed in the absence of any haptic feedback about the tissue.

Accordingly, there is a need in the art for a surgical assist device that will improve the visualization of the tissue at the site so that a surgeon can more quickly and effectively evaluate the progress of the procedure.

BRIEF SUMMARY OF THE INVENTION

The present invention is a medical device that emits sufficient fluorescence to penetrate surrounding tissue to a predetermined depth so that a surgeon can more clearly visualize the presence and quality of different types of tissue within the illuminated depth. The medical device may comprise a polymer and a near infrared fluorescent dye embedded in the polymer such that excitation of the near infrared fluorescent dye will produce near infrared fluorescence capable of penetrating human tissue to a predetermined depth. The predetermined depth is about ten millimeters and is achieved by the amount of fluorescence produced by indocyanine dye in ethanol at a concentration of four parts per million. The medical device may be a bowel sizer having a head that is at least partially formed from the polymer embedded with the near infrared fluorescent dye. The medical device may be a vaginal manipulator at least partially formed from the polymer embedded with the near infrared fluorescent dye. The medical device may be a uterine manipulator having a cup that is at least partially formed from the polymer embedded with near infrared fluorescent dye. The cup may include a guide ridge formed from the polymer embedded with near infrared fluorescent dye. The medical device may be a ureteral catheter formed from the polymer embedded with the near infrared fluorescent dye. The medical device may be an endotracheal tube formed from the polymer embedded with the near infrared fluorescent dye. The medical device may be a feeding tube formed from the polymer embedded with the near infrared fluorescent dye. The near infrared fluorescent dye may indocyanine green. The polymer may be polycaprolactone. The medical device may include an enhancer embedded in the polymer along with the near infrared fluorescent dye. The enhancer may be milk powder.

The present invention also comprise a method of visualizing tissue during a surgical procedure where the device of the present invention is positioned under the tissue to be visualized and excited with a first frequency of near infrared radiation. A second frequency of near infrared radiation that is emitted by the device is detected and displayed for viewing. The second frequency of near infrared radiation emitted by the device penetrates the tissue to a depth of about ten millimeters. The displaying the second frequency of near infrared radiation emitted by the device for viewing comprises may comprise displaying the second frequency of near infrared radiation in combination with the visual spectrum. The step of exciting the device with a first frequency of near infrared radiation includes modulation of at least one of the intensity, the angle of incidence, and the duty cycle of the source of near infrared radiation.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 14 is a side plan view of a near infrared polymer based surgical uterine manipulator;

FIG. 15 is a cross sectional view of a near infrared polymer based surgical uterine manipulator taken along line B-B of FIG. 14;

DETAILED DESCRIPTION OF THE INVENTION

Figure 1:
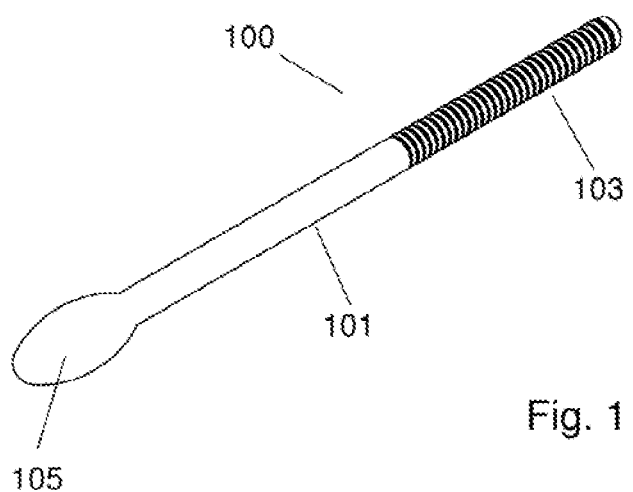
FIG. 1 is a perspective view of a near infrared polymer based surgical sizer of the present invention.
Figure 2:
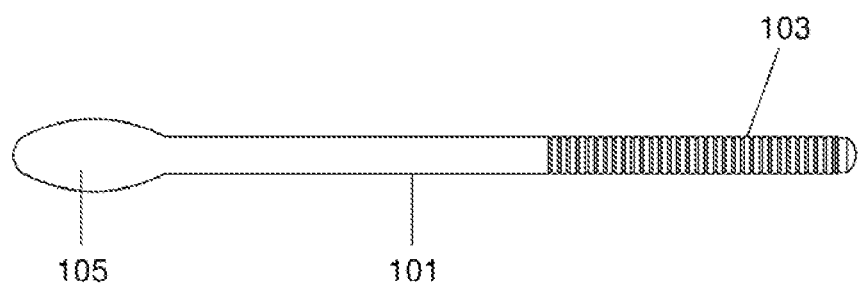
FIG. 2 is a plan view of the surgical sizer of FIG. 1.
Figure 3:
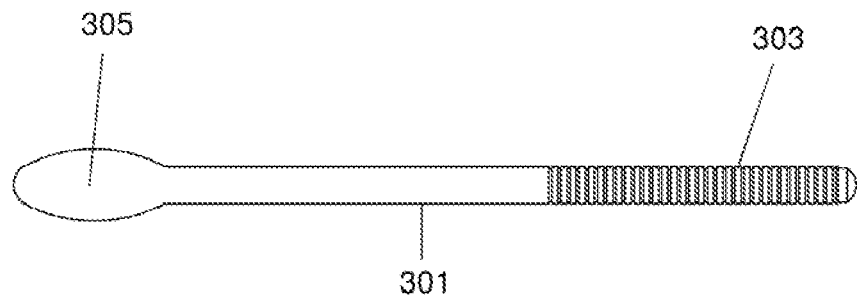
FIG. 3 is a plan view of a near infrared polymer based surgical bowel sizer according to the present invention.
Figure 4:
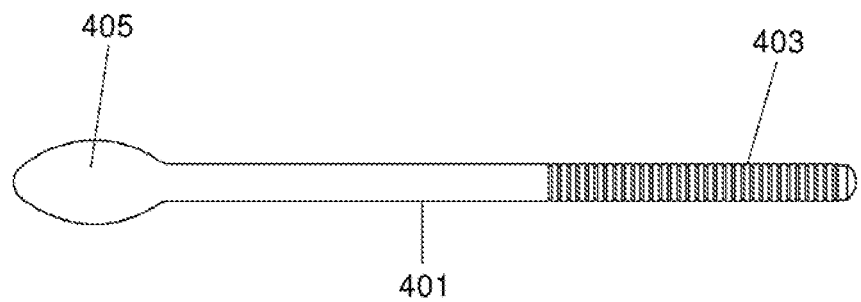
FIG. 4 is a plan view of another near infrared polymer based surgical bowel sizer according to the present invention.
Figure 5:
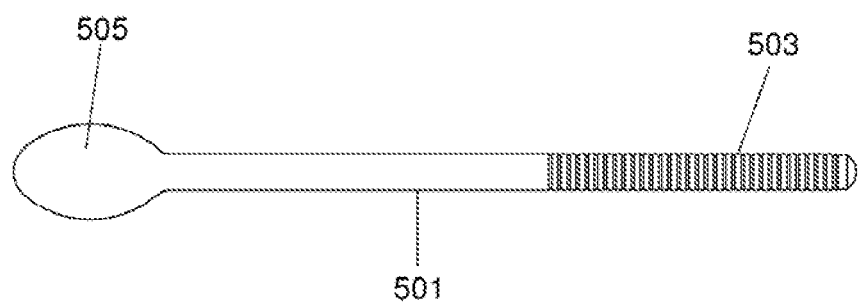
FIG. 5 is a plan view of a further near infrared polymer based surgical bowel sizer according to the present invention.
Figure 6:
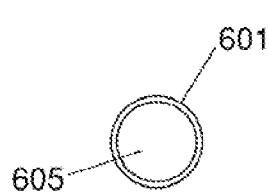
FIG. 6 is an end view of a near infrared polymer based surgical vaginal and rectal manipulator of the present invention.
Figure 7:
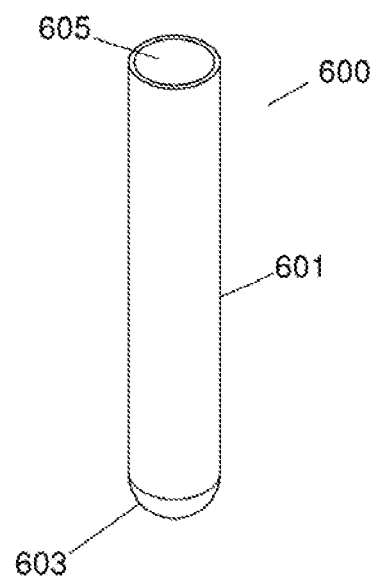
FIG. 7 is a perspective view of a near infrared polymer based surgical vaginal and rectal manipulator of the present invention.
Figure 8:
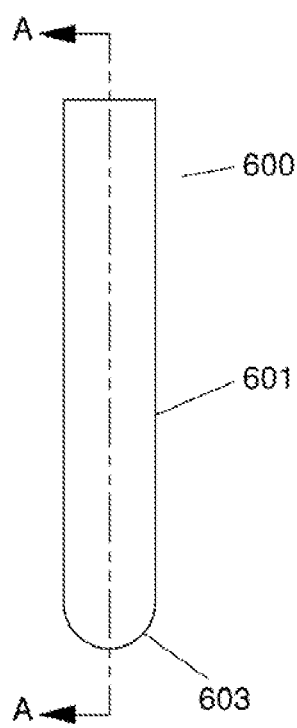
FIG. 8 is a side view of a cross sectional view of a near infrared polymer based surgical vaginal and rectal manipulator.
Figure 9:
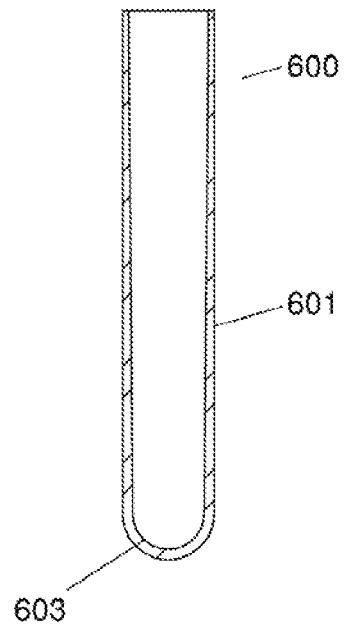
FIG. 9 is cross-sectional view of the near infrared polymer based surgical vaginal and rectal manipulator taken along line A-A of FIG. 8.
Figure 10:
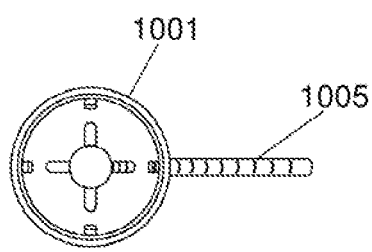
FIG. 10 is an end view of a near infrared polymer based surgical uterine manipulator.
Figure 11:
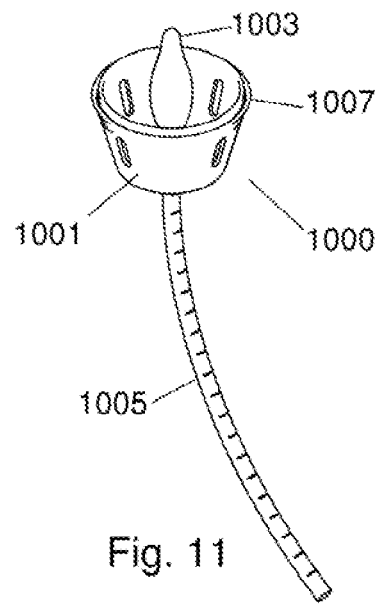
FIG. 11 is a perspective view of the near infrared polymer based surgical uterine manipulator.
Figure 12:
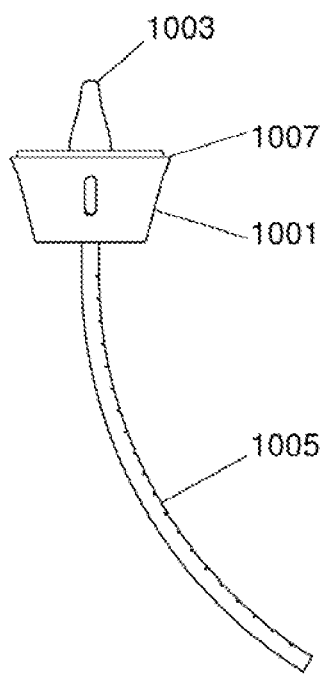
FIG. 12 is a side view of a near infrared polymer based surgical uterine manipulator.
Figure 13:
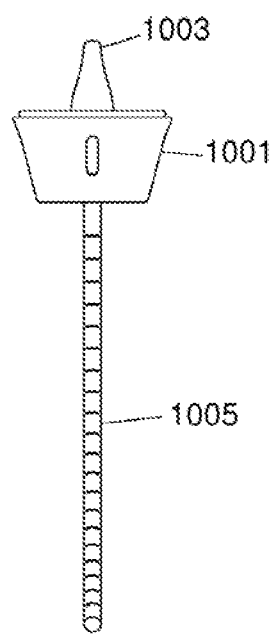
FIG. 13 is a plan view of a near infrared polymer based surgical uterine manipulator.

Referring to the figures, wherein like numeral refer to like parts throughout, there is seen in FIG. 1 an example medical device 100 that may be formed according to the present invention from, at least in part, a near infrared (NIR) polymer, for visualization of the surrounding tissue. More specifically, the present invention comprises the formation and use of a surgical assist device that is embedded with a fluorescent dye or dye mixture, such as indocyanine green dye (ICG), by including the fluorescent dye in the polymer used to form the device. The dye may be modified by the addition of a fluorescence enhancer to attenuate the amount and quality of the fluorescence. The resulting fluorescent medical device may then be used to provide enhanced imaging of the surrounding tissue during a surgical procedure, such as a robotically assisted surgery, by positioning the device under the tissue in the surgical field, illuminating the device with NIR illumination, and then visualizing the surrounding tissue in the NIR spectrum.

For example, robotically assisted surgical systems include NIR sources and detectors that may be used to provide fluorescence from a device according to the present invention. The use of devices according to the present invention, such as bowel sizer 100 and other devices described herein, produce unexpected results with respect to visualization of surrounding tissue and improvement of surgical procedures. A device according to the present invention allows for a rapid and clear determination of surrounding tissue depth, an identification of tissue inhomogeneity, the detection of masses or tissue irregularities, improved visualization of anatomical holes and tears, and enhanced contrast of the surgical field. As a result, surgical procedures performed with the use of a device according to the present invention can be performed more quickly and more effectively, thereby reducing the amount of time that a patient spends in surgery, improving the efficacy of the procedure, reducing recovery time, providing enhanced surgical decision capacity, and avoiding surgical errors.

The fluorescent dye embedded in the medical device may be any fluorescent dye that can produce an acceptable amount of fluorescence, either alone or when combined with a fluorescence enhancer, so that when the dye is incorporated into a medically acceptable polymer and then shaped into a medical device according to the present invention it produces a desired tissue penetration, such as about 10 millimeters. The amount of fluorescence produced by an exemplary NIR medical device that will penetrate tissue to a depth of about 10 millimeters, and thus provide the enhanced tissue illumination of the invention, is approximately equal to the amount of fluorescence produced by a solution of ICG in ethanol at a concentration of four (4) parts per million. As ICG is well known, the amount of fluorescence produced by a solution of ICG in ethanol at a concentration of four (4) parts per million provides an objective benchmark against which the fluorescence of other dyes and dye-polymer mixtures may be evaluated to determine whether they will produce the predetermined amount of fluorescence needed for the present invention. Table 1 below has a list of various dye and substrate combinations that may be used for a medical device according to the present invention along with their relative fluorescence as compared to a solution of 4 ppm ICG in ethanol.

TABLE 1

| Dye | Substrate | ppm | Relative Fluorescence |
| --- | --- | --- | --- |
| ICG | Ethanol | 4 | 100 |
| ICG | Steralloy2380 | 20 | 92 |
| ICG | Acrylonitrile butadiene styrene | 20 | 41 |
| ICG | Polytetrafluoroethylene | 80 | 77 |
| Epolight 5768 | Polycarbonate | 8 | 210 |

It should be recognized by those of skill in the art that the particular concentration of dye embedded into a polymer may be varied according to the present invention to produce different amounts of fluorescence, which may then be attenuated to produce the requisite amount of fluorescence. For example, a dye with greater near infrared fluorescence than ICG may be used in less concentration with the same excitation delivered during use, or in the same quantity with less excitation delivered during use, while still achieving sufficient tissue penetration to enable a surgeon to distinguish between tissue layers and types up to at least ten millimeters as the resulting fluorescence will be approximately the same. It should be recognized that a medical device according to the present invention may be designed to fluoresce to a lesser depth of penetration, such as seven millimeters, for a specific application where that amount of tissue penetration is sufficient for that specific application. Similarly, a medical device according to the present invention may be designed to fluoresce to a greater depth of penetration, such as twelve millimeters, for a specific application where that amount of tissue penetration is optimal for that specific surgical procedure.

The fluorophore may be embedded directly into a medical acceptable polymer, or may be enhanced to improve and control the fluorescence of the fluorophore selected for enhancing the medical device so that the fluorescence provides the enhanced visualization of the surrounding tissue of the present invention. ICG, for example, is fluorescent in aqueous solutions below 50 µg/ml and quenches at higher concentrations. ICG has been successfully tested for the present invention by enhancing and embedding the dye in polymers that are regarded or accepted for safe use in surgery. ICG absorbs near infrared light between 600 nm and 900 nm in wavelength, with an optimal excitation wavelength of 805 nm. ICG will emit fluorescence between 750 nm and 950 nm in wavelength with an optimal emission wavelength of 835 nm. Excitation of a device that has been embedded with ICG may be performed with a laser having a laser diode has a power output, for example, of 3 watts at a wavelength of 806 nm. The laser output may be decollimated to spread the laser light over the enough of the surgical field of view that includes the ICG embedded device. The near infrared light emitted from an ICG embedded device will penetrate the surrounding tissue and blood so that, when detected by a NIR imaging system, the fluorescent device provides a wealth of information about tissue depth, tissue density, and tissue inhomogeneity. The quantum efficiency of ICG is enhanced over 1000 fold after intravenous injection or diluted in blood, with peak fluorescence at ~10 µg/ml. ICG is intensely fluorescent in methanol, ethanol, and DMSO. It should be recognized that shortwave infrared (SWIR) with wavelengths between 1,100 and 3,000 nanometers may be substitutes for NIR using SWIR dyes and associated detectors.

When embedded in a polymer, the fluorescence that results may be insufficient to properly image the surrounding tissue. Accordingly, the present invention may include the enhancement of ICG through the use of organic and inorganic compounds, such as milk, dried milk, tapioca, gelatin, pasta, whey, semolina flour, and Intralipid, that will enhance and modify the amount of distribution of the fluorescence of the ICG embedded device to provide the unexpected benefits of the present invention, such as the enhanced visual depth of field and the ability to easily visualize and determine tissue thicknesses and compositions during a medical procedure. More specifically, organic and inorganic materials may be added to the polymer and ICG mixture to increase the amount of fluorescence and to produce light scatter conditions for optimal fluorescence imaging. With no scattering, excitation energy will pass through the material of the ICG embedded device. With too much scattering, all of the excitation energy is reflected at the surface of ICG embedded device so that images from the fluorescence are oversaturated and impossible to assess. As a result, medical devices according to the present invention may be embedded with optimum quantities of an enhanced dye produce an effective amount of fluorescence based on both the medical application and the particular polymer or material chosen for the medical device.

As described above, a medical device made from an NIR polymer according to the present invention will produce sufficient fluorescence to allow visualization of surrounding human tissue of up to an optimum amount for a particular surgical procedure. For example, in the procedures described herein, tissue penetration of near infrared fluorescence from a medical device manufactured from a polymer embedded with a fluorophore according to the present invention to a depth of about 10 millimeters (1 centimeter) revealed information about the tissue that allowed for improved surgical decision making. The depth of penetration provides visual information about the illuminated tissue within that depth, such as the quality of the tissue, thicknesses of different types of layers of tissue, scarring, etc. A surgeon may thus readily determine relative tissue depth, identify tissue inhomogeneity, detect masses or tissue irregularities, pinpoint anatomical holes, or visualize tears. As a result, medical procedures requiring that the surgeon distinguish between tissue types or tissue consistencies within the range of zero to 10 millimeters in thickness, such as separation of a bladder from the connective tissue during a sacrocolpopexy, a cystectomy, or an endometriosis/oncologic debulking procedure, can be more clearly visualized by positioning the NIR polymer medical device proximately to the tissue to be visualized, illuminating the medical device with the appropriate stimulation wavelength, and then displaying the emitted fluorescence visually to the surgeon. The emitted fluorescence allows the surgeon to rapidly identify and locate the appropriate tissue or tissue layers involved in the procedure, thereby improving real-time surgical decisions. The present invention thus helps reduce the time taken for surgical procedures while improving the surgical outcome. Less time in surgery and improved quality of surgery decreases the risks associated with surgery, increases patient recovery times, and increases the likelihood of successful surgeries.

The detection and visualization of NIR fluorescence emission from an ICG embedded device may be performed with a CCD, CMOS, EMCCD, InGaAS (SWIR) or other optical sensor capable of detecting the emittance wavelength. The sensor may be associated with a robotically assisted surgical system or provided as part of a separate NIR imaging system. For example, the Firefly NIRF imaging subsystem (available from Intuitive Surgical), a component of the da Vinci minimally invasive robotic surgery system, may be used to detect and view fluorescence by a device according to the present invention. Similarly, conventional NIR microscopes and imaging systems, such as the Zeiss Pentero OR microscope system with NIRF capability, may also be used in combination with the present invention, as well as laparoscopic systems such as the Storz, Novadaq, and Stryker laparoscopic systems having NIRF capabilities. Florescence images formed from the use of the ICG embedded device provide a user with enhanced surgical contrast (particularly with robotically-assisted surgeries or other minimally invasive close quarters surgical procedures) that assist the user in the detection of masses and other tissue irregularities.

The received NIR image may be digitized and combined with other digital data such as a full spectrum image, ultrasound image, x-ray image, or the like, and using various digital processing techniques an enhanced image of the anatomical area of interest is produced, providing information and visualization of below surface tissue that has heretofore not been possible. This enhanced field of vision can be delivered to a surgeon in real time, providing better surgical guidance, decision making and even a dimension of virtual haptics that is not currently available with robotically assisted surgical systems and equipment. In addition, subsurface tissue information may also be converted using digital signal processing techniques to haptic feedback at the surgical control level, providing, for example a vibration, pressure, resistance, or other feedback to the surgeon at the control points during robotically assisted surgeries or other advanced technology surgical devices and systems. In some procedures, for example, it is preferable for a surgeon to begin dissection in an area where the least amount of tissue is present. An ICG embedded device according to the present invention can be used to selectively illuminate different depth tissue to convey to the surgeon the area of least tissue presence.

NIR polymers may be formed into the desired medical device using conventional polymer processing. For example, if PCL is used as the base polymer, it may be rotated in heated tubes to ensure a uniform distribution of the NIR dye and then extruded using twin screw polymer extrusion machines. Similarly, twin hopper instruments that feeds solid feedstock into a heated zone where melting and mixing occurs may be used to produce NIR polymer stock, such as pellets, filaments or tubing, that can then be extruded, injected, or blow molded to form the shape of the desited medical device to be enhanced according to the present invention. Alternatively, the NTR polymer may be configured as a filament stock for a 3D printer such as the MakerBot.

Various medical devices may be enhanced according to the present invention to provide an enhanced visual depth of field and determination of tissue thickness and composition, thereby improving the accuracy, efficacy, and time needed for surgical procedures associated with those medical devices. For example, bowel sizers, vaginal manipulators, rectal manipulators, uterine manipulators, bougie devices, ureteral stents, urethral catheters, endotracheal tubes, endogastric feeding tubes, hemostatic agents, sutures, clips, staples, screws, probes, surgical needles, etc. may be used in connection with the present invention to provide near infrared fluorescence penetration into surrounding tissue. Devices according to the present invention may be used in various surgical procedures where visualization of the surrounding tissue provides a benefit to the surgeon, such as oncologic surgeries, removal/identification of endometriosis, or pelvic reconstruction procedures.

Example 1

To prepare indocyanine green (ICG) for use in an exemplary medical device, ethanol was added to indocyanine green. 10 ml. of ethanol was added to 25 mg of ICG and mixed gently. Steralloy 2380A resin and Steralloy 2380B curative were mixed in the proportion of 50 ml. of 2380B with 200 ml. of 2380A. 2 ml. of the ethanol and ICG solution were added to the resin and curative combination. To provide a resulting surgical tool that has the proper aesthetic qualities, Steralloy PD-7 MP Opaque white color dispersion was added to the mixture. The ICG solution and color dispersion was added to the Steralloy 2380B curative and the resulting mixture was added to the Steralloy 2380A resin. The resulting mixture (approximately 20 parts per million of ICG) was poured into a mold to cast the resulting surgical device. It should recognized that other approaches, such as adding ICG or an ICG solution to a plastic feedstock prior to injection molding, blow molding, extruding, 3D printing, or the like, may also be employed.

Example 2

An enhanced NIR polymer was produced according to the present invention by embedding an enhanced NIR powder formed from ICG and milk powder into poly(caprolactone) (PCL; 2-oxypanone), a biocompatible thermoplastic material that is often used in FDA-approved devices such as suture materials, e.g. Monocryl (Ethicon), and then molding the ICG embedded polymer into the desired shape for the medical device. Milk powder was selected over semolina as NIR powder formed from ICG and semolina resulted in a coarse grain and some undesirable properties when used repeatedly under different heating conditions and with repeated water immersion. By contrast, when an ICG an DMSO mixture was used, the resulting polymer was only sufficient fluorescent for about 24 hours as the DMSO dissipated from the material. To achieve the finer grain powder, 50 g of dry evaporated milk was rehydrated with about 100 cc of neat ethanol and ~500 ml of water was then added to 2.5 mg of ICG in 1 ml of water from a frozen stock solution. This achieved a light green tinted solution, which was then poured into a shallow pan, evaporated to dryness, mechanically pulverized, and passed through a sieve. The final product was ~50 ppm ICG in evaporated milk powder (50 mg/kg). This resulting NIRF powder was added at 1%, 5% and 10% (10,000-100,000 ppm) by weight to polycaprolactone (InstaMorph) in a silicone container in a glassware drying oven and repeatedly massaged and passed through rollers to achieve mixing and sheets of material.

As an alternative to evaporated milk powder, which is conventionally produced by spray drying that yields a controllable particulate size based on solute concentration, other materials may be used to enhance the quantum efficiency of the fluorescent dye, such as starches, amino acids, proteins, oils, emulsions, micelles, food colors, plasticizers or other agents already approved for human use may be formed into particulate for mixing with ICG and incorporation into a polymer to produce the enhanced NIR polymer. For example, cornstarch may be pre-bound to ICG and then embedded into a polymer according to the present invention.

Example 3

FIGS. 1-5 illustrate a surgical visualization and medical imaging device in the form of a surgical bowel sizer 100. Bowel sizer 100 comprises a shaft 101, a grip 103 and a head 105. Shaft 101 may be of various lengths dependent on the surgical task required. Head 105 may be, for example, in the range of 25-33 millimeters in length. Bowl sizer 100 is made, at least in part, from an NIR polymer according to the present invention. For example, the entire bowler 100, just head 105, or just a portion of head 105 may be formed from the NIR polymer for near infrared fluorescence when exposed to near infrared radiation.

Example 4

FIGS. 6-9 depict a surgical visualization and medical imaging device in the form of a surgical vaginal manipulator 600 formed from a fluorescent polymer according to the present invention. Surgical vaginal manipulator 600 comprises a cylindrical form 601 having an end 603 and a core 605. Core 605 may be made from the same material as the remainder of the surgical vaginal manipulator, or in some embodiments may be hollow or otherwise filled with an alternate material. Vaginal manipulator 600 comprises, at least in part, an NIR polymer according to the present invention for near infrared fluorescence of vaginal manipulator 600 when exposed to near infrared radiation.

Example 5

FIGS. 10-15 depict a surgical uterine manipulator 1000. Uterine manipulator 1000 comprises a cup 1001, a guide ridge 1007 circumscribing the circumference of cup 1001, and an inflatable balloon 1003 positioned within cup 1001. A shaft 1005 is operatively coupled to cup 1001. In some embodiments, shaft 1005 has graduation marks, and may also comprise a conduit or opening to deliver air or other gas to inflatable balloon 1003. Uterine manipulator 1000 comprises, at least in part, an NIR polymer according to the present invention. For example, cup 1001 may be formed entirely from the NIR polymer. Alternatively, just guide ridge 1007 may be formed from the NIR polymer for near infrared fluorescence when exposed to near infrared radiation.

Example 6

Figure 16:
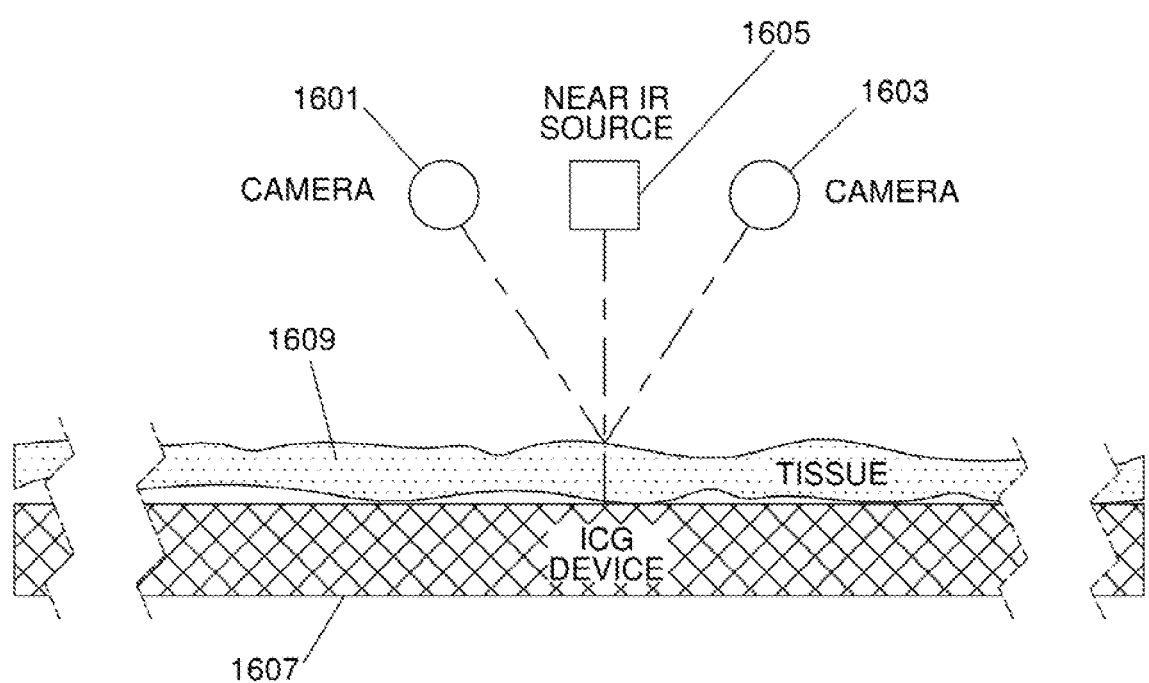
FIG. 16 is a diagram of a surgical visualization and medical imaging system including a near infrared polymer based medical device according to the present invention.

FIG. 16 illustrates a surgical visualization and medical imaging system 1600 comprising a near infrared (NIR) source 1605 along with multiple cameras 1601 and 1603 for three-dimensional imaging in the visual and NIR spectrums of tissue 1609 under which a NIR polymer based medical device 1607 has been positioned. It should be recognized that multiple cameras may be used, with different camera for the visual and NIR spectrums, or combined cameras that can detect and produce images in both the visual and NIR spectrums simultaneously with the particular NIR wavelengths being selected based on the composition of the NIR polymer used in device 1607. For example, a camera that can detect fluorescence between 750 nm and 950 nm in wavelength, with an optimal or preferred wavelength of 835 nm, would be suitable for ICG based NIR polymers.

Illumination from NIR source 1605 may be directed onto the field of view and, as a result, medical device 1607 so that device 1607 fluoresces. NIR source 1605 may produce laser emitting excitation energy in the range of 600 nm to 900 nm in wavelength that is decollimated to spread the laser light over the surgical field of view, with the resulting fluorescence of device 1607 having an excitation wavelength of 805 or 806 nm. NIR source 1605 source may have an angle of incidence adjustment that is controlled by a servo or piezoelectric motor. NIR source 1605 may also have a duty cycle adjustment.

The resulting fluorescence provides enhanced visualization of tissue 1609 as discussed above when detected by cameras 1601 and 1603 and displayed for a surgeon. System 1600 may be embodied as party of a robotically assisted surgical system with the various components attached to or formed as part of a robotic appendage or a support or structure thereof with device 1607 coupled to or even formed as part of a robotic arm of system 1600. The system of the present invention may further include the ICG based surgical device itself.

Cameras 1601 used for imaging of NIR polymer medical device 1607 may be coupled to digital signal processors and imaging systems for further processing of captured images or video, such as attenuation of intensity, gain, etc. so that a user can modify the displayed image for maximum effectiveness.

Figure 17:
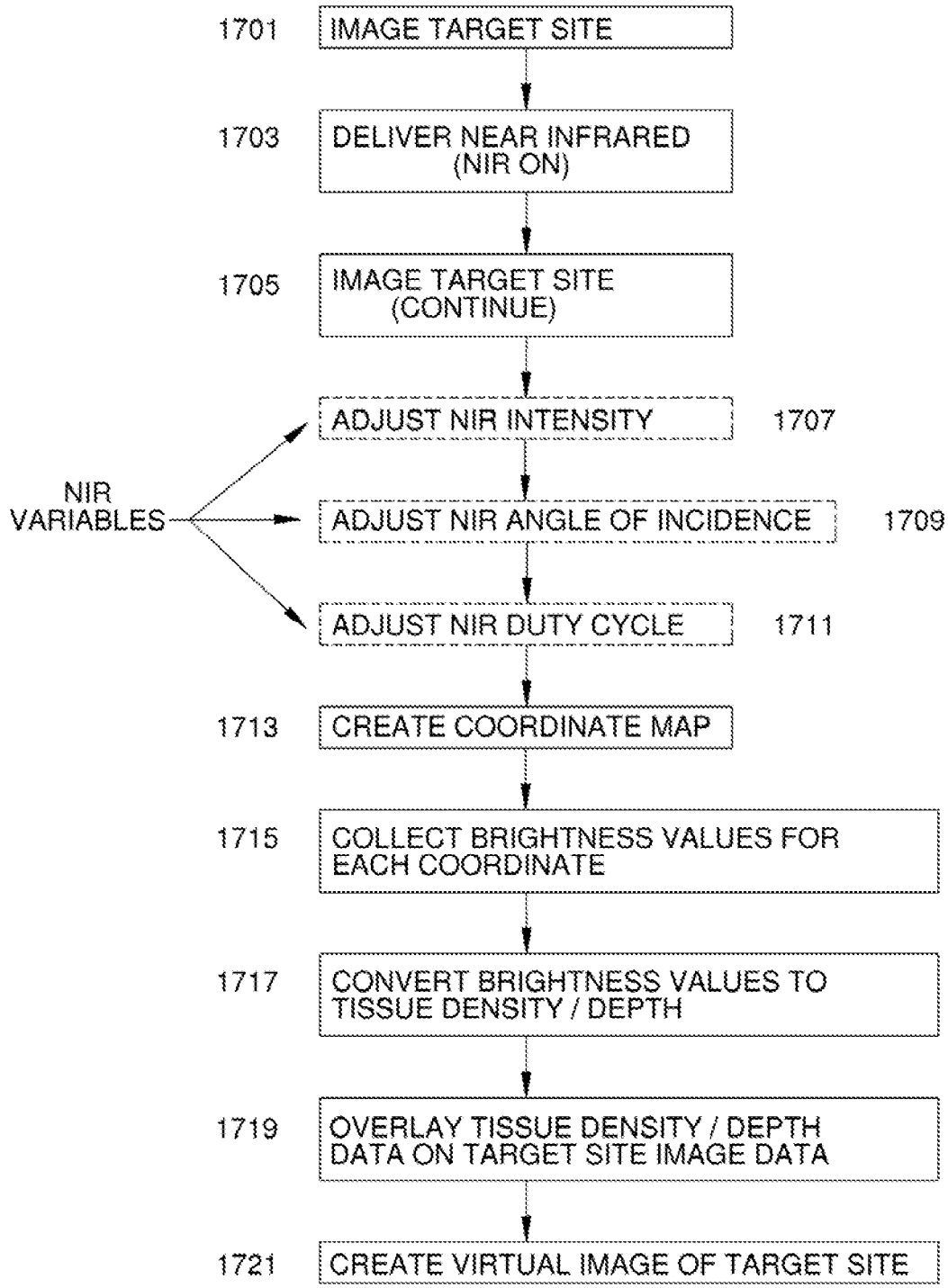
FIG. 17 is a flowchart of surgical visualization and medical imaging method according to the present invention.

FIG. 17 is a flowchart of method of improving the visualization of tissue during a surgery using an NIR polymer medical device according to the present invention. In step 1701, a surgical target site is imaged. Imaging may be performed by full spectrum or near infrared only detection with sensors such as CCD or CMOS arrays. NIR radiation in the wavelength range of between 600 nm and 900 nm, and preferably 805 or 806 nm, is delivered by, for example, a laser NIR source in step 1703. The laser source may be decollimated or otherwise dispersed to spread the infrared light over the surgical field of view or field of interest. In step 1705, the target site or surgical field of interest is imaged further. Imaging continues in real time, and may be recorded for further processing, throughout the surgical procedure to provide enhanced visualization to the attending surgeon. For specific visualization and digital imaging needs, the source of near infrared radiation may be optionally adjusted in intensity 1707, angle of incidence 1709, or duty cycle 1711. These NIR variables may be under software control to allow for specified diagnostics or imaging, or may be under the manual control of the surgeon to aid in real time visualization at the control and direction of the surgeon.

It can be envisioned that specific test sequences may be developed under software control to detect tissue anomalies such as tears, unusual masses, and the like. For example, a specific angle of incidence with pulsed near infrared excitation at a specified duty cycle may be optimal for detecting a certain tissue anomaly such as an atypical mass of a certain density that could be indicative of a certain medical condition. A coordinate map of the surgical field of view may be created on a computer system in step 1713, such system having a processor, memory and computer readable media or access thereof. Coordinates are assigned to each location on the created coordinate map. In some embodiments of the present invention, resolution may be defined by the system itself, or the user or other operator of the system. This process of coordinate assignment may be real time or near real time throughout the surgical procedure, with digital signal processing techniques used for coordinate assignment, reassignment, retention and processing. Through the use of the NIR sensor(s) or cameras, brightness values of near infrared emissions from the ICG surgical device of the present invention are collected and processed. In step 1717, for example, these collected brightness values are converted to relative tissue depth (thickness) and tissue density values. These relative tissue depth and tissue density values for each coordinate are then used to create a virtual image of the surgical field of view, and an image of the surgical field of view is added to or otherwise displayed with the virtual image of the surgical field of view that uses near infrared data. Thus, in step 1719 the created virtual image of tissue density and depth is overlaid with an image of the surgical field of view (target site image data) to create a virtual image of the target site 1721 that is enhanced or otherwise improved with tissue depth and density imaging that has heretofore not been possible with surgical imaging systems. The combinational steps of adding a NIR image to the image of the surgical field of view may also include the use of imaging from other sources such as ultrasound, X-ray radiography and fluoroscopy, magnetic resonance imaging (MRI), thermography, scintigraphy, elastography, tactile imaging, photoacoustic imaging, echocardiography, positron emission tomography, single photon emission tomography, endoscopy, and the like.

Figure 18:
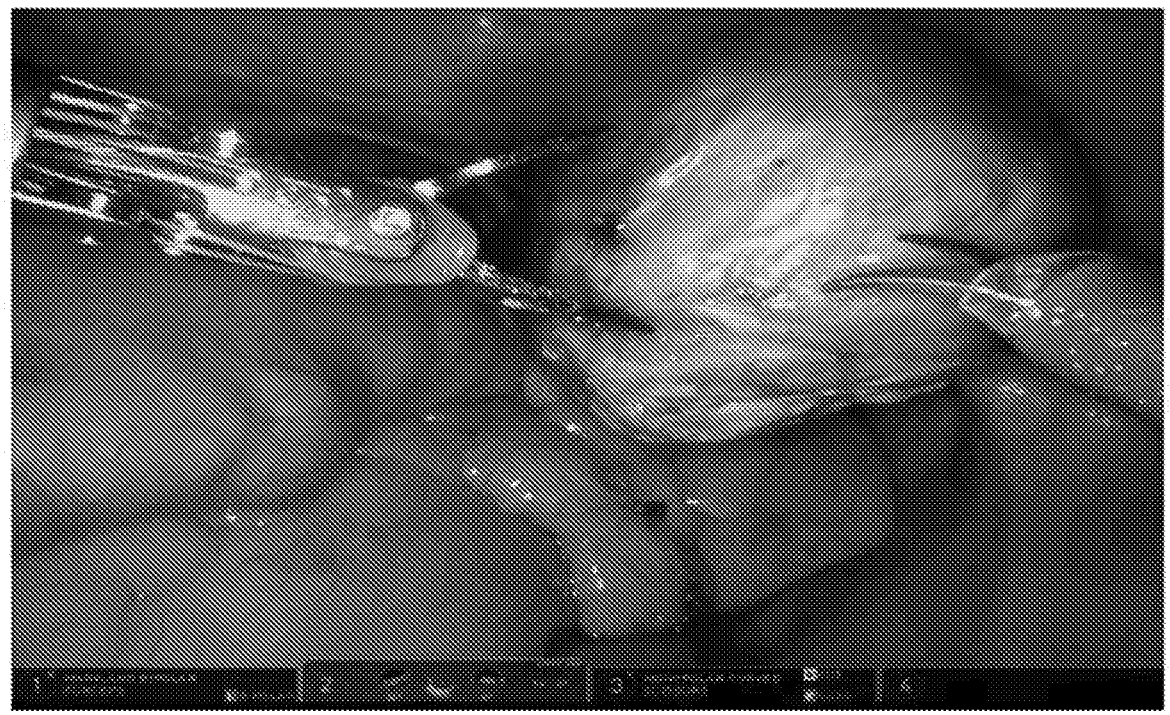
FIG. 18 is an NIR image of a surgical field of view in a sacrocolpopexy procedure using a robotically assisted surgical system and employing an NIR polymer medical device according to the present invention.
Figure 19:
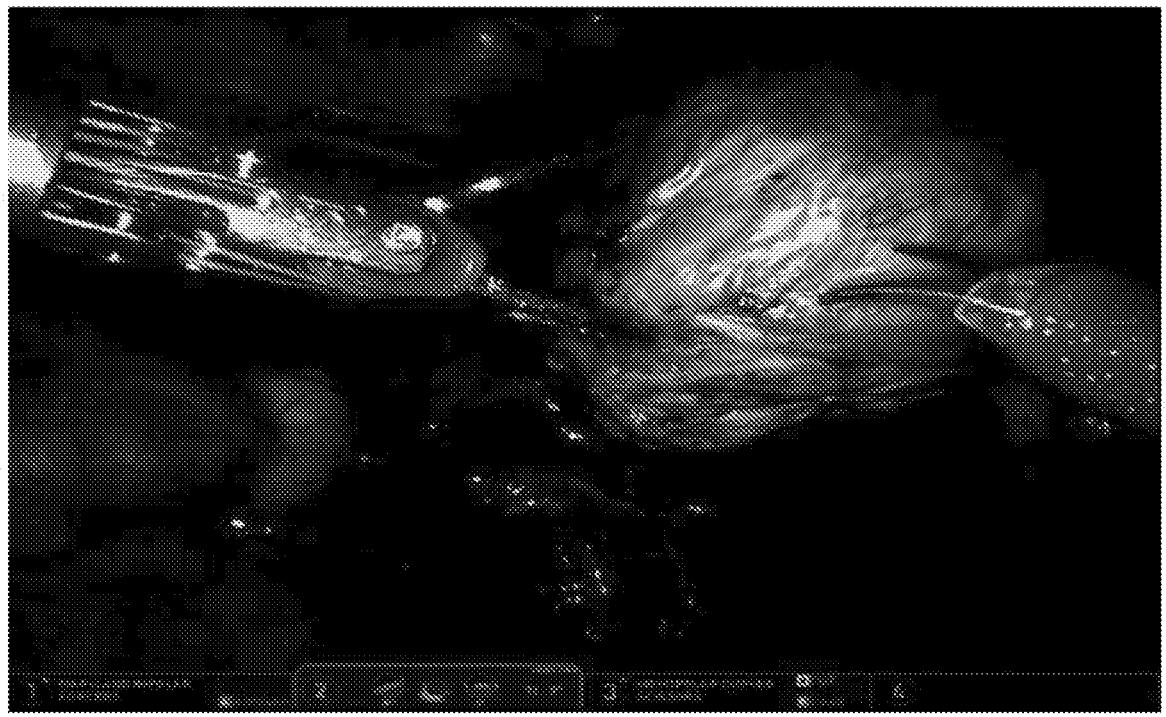
FIG. 19 is an NIR image of an NIR polymer medical device receiving excitation energy from a near infrared source and emitting near infrared light that can be seen in the imaging system.
Figure 20:
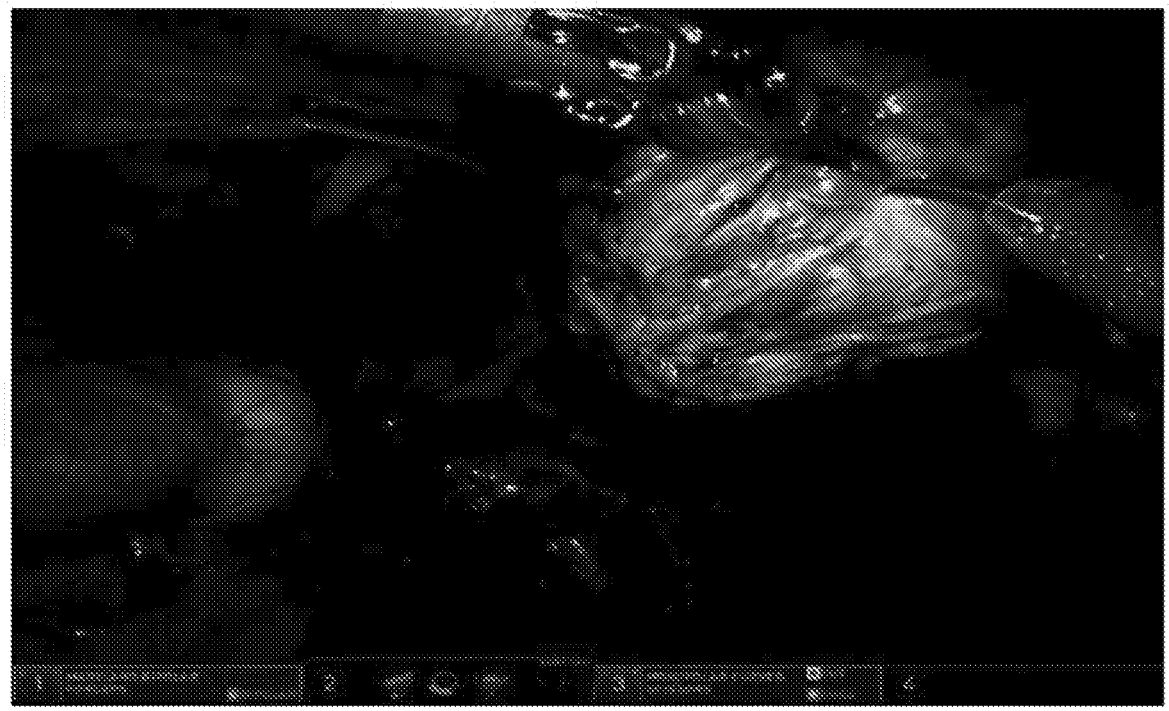
FIG. 20 is an NIR image of the identification of an area with the least amount of tissue as a surgical starting point through the use of a near infrared polymer based medical device according to the present invention.
Figure 21:
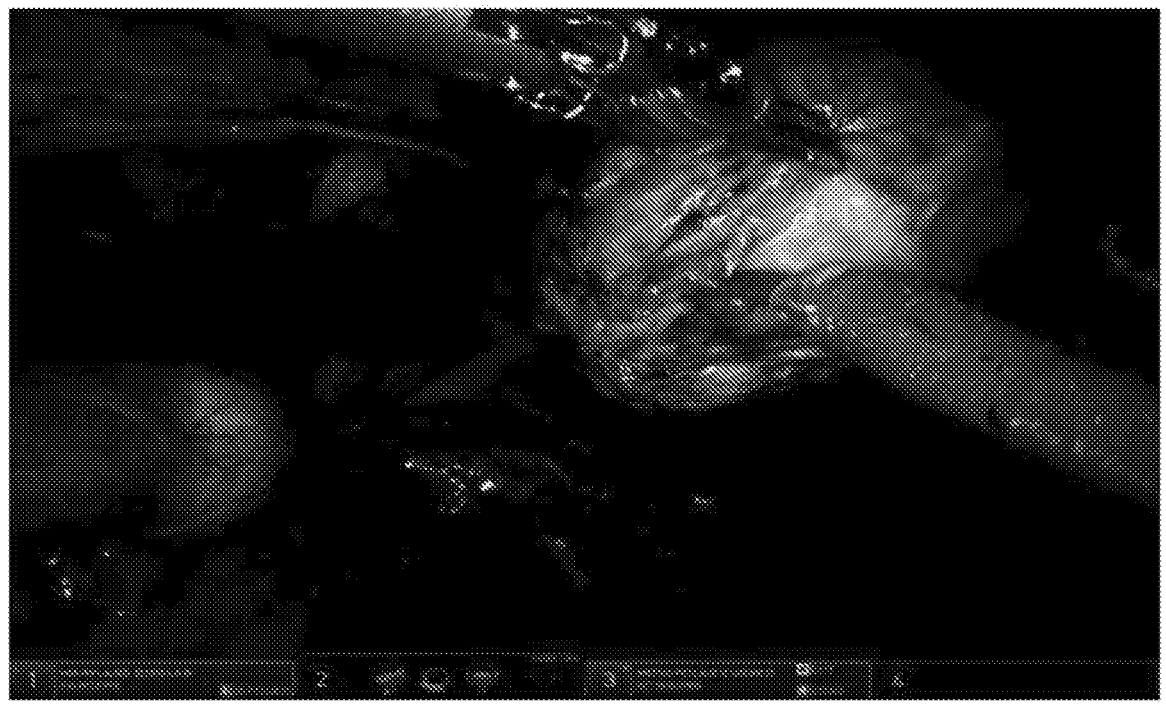
FIG. 21 is an NIR image of the start of the incision as enhanced by a near infrared polymer based medical device according to the present invention.
Figure 22:
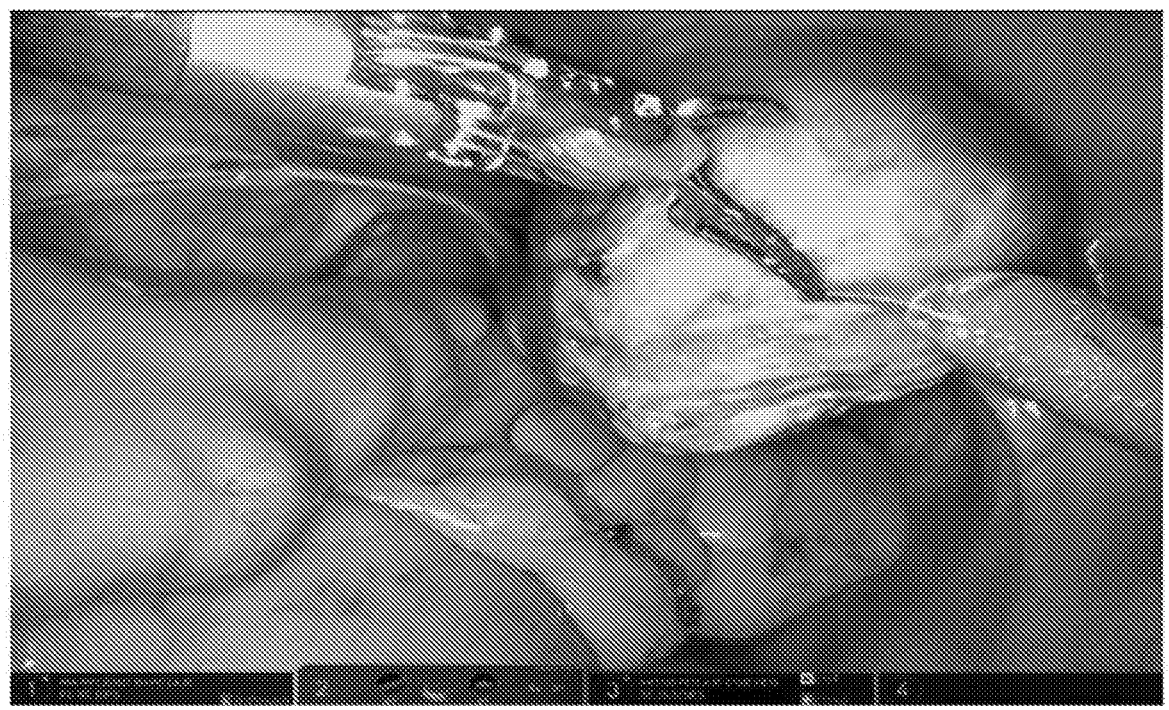
FIG. 22 is a full spectrum image of the procedure of FIGS. 18 through 21.
Figure 23:
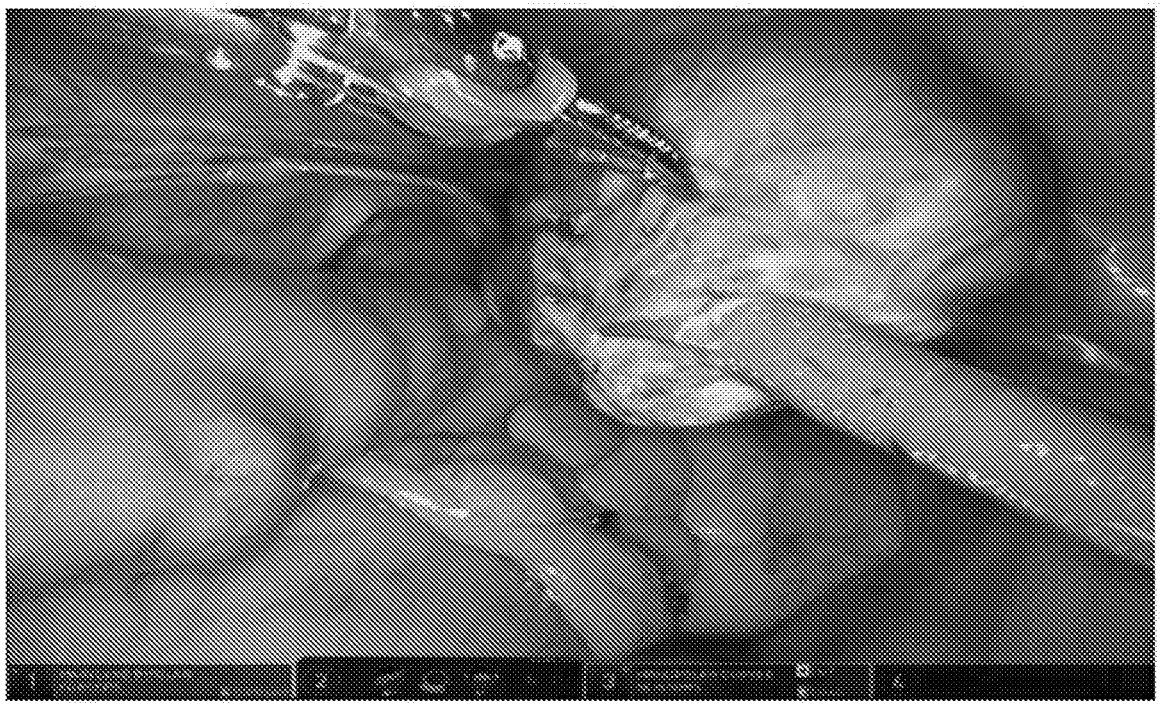

FIGS. 18-23 are a series of sequential images taken during the use of an NIR polymer medical device according to the present invention during a sacrocolpopexy procedure performed with a robotically assisted surgical system. The most fluorescent area shown is the area with the least amount of tissue between the NTR polymer medical device and the operative field. In the illustrations depicted, the area with the least amount of tissue, as evident by the intensity of emitted light from the NTR polymer medical device, is the area in which the surgeon began to develop a bladder flap, thereby giving the surgeon a visual starting point. FIG. 18 shows the surgical field of view (target site). FIG. 19 shows the NIR polymer medical device receiving excitation energy from a near infrared source and emitting near infrared light that can be seen in the imaging system as a green glow, with surrounding tissue in black and white. FIG. 20 shows identification of the area with the least amount of tissue as a surgical starting point. FIG. 21, again under near infrared, shows the start of the incision. FIGS. 22 and 23 show the procedure continuing under full spectrum illumination.

These images represent an exemplary surgical procedure that can benefit from the devices, systems and methods of the present invention. More specifically, the ability of invention, regardless of its shape, to provide fluorescence that penetrates through a predetermined amount of tissue is an important feature. This penetration provides information about the relative tissue depth, which is the millimeter by millimeter contrast of adjacent tissues in comparison to each other, as well as the consistency of the tissue. For example, tissue that includes scar tissue will be illuminated by the fluorescence differently than non-scared tissue due to differences in tissue density. The NTR visual information provided by the present invention is particularly important when used in connection with robotic surgeries, such as surgeries using the daVinci robot, because the surgeon does not have the ability to feel the quality of the tissue and must instead rely on visual clues.

Because the fluorescence illuminates the contrast in the tissue, the present invention can also be used for finding abnormal or heterogeneous areas of tissue. For example, tissue that is denser or thicker than surrounding tissue rendered more visible with the present invention. For example, endometriosis on a bladder, vagina, rectum or ureter will be highlighted by the difference in illumination penetration. As great care must be taken when removing endometrial tissue from the underlying tissue without damaging the underlying tissue, the present invention can be used to more clearly delineate the different tissue and thus improve the surgical outcome. Similarly, abnormal or cancerous tissue, such as recurrent endometrial cancer most commonly found at the vaginal cuff, can be more easily visualized with the present invention. The present invention may also be used to help identify inadvertently damages or injured tissue, thereby avoiding the need for manual inspection or the use of visible liquids and allowing for more rapid remediation.

In a first aspect, the present invention is a surgical visualization and medical imaging device comprising a surgical bowel sizer comprising a shaft, a grip, and a functional end, the surgical bowel sizer comprising a plastic containing indocyanine green dye in proportions suitable for near infrared fluorescence of the surgical bowel sizer when exposed to near infrared radiation.

In a second aspect, the surgical visualization and medical imaging device is made from a biocompatible thermoplastic material.

In a third aspect, the surgical visualization and medical imaging device of claim is made from polycaprolactone (PCL; 2-oxypanone).

In a fourth aspect, the surgical visualization and medical imaging device comprises an organic material.

In a fifth aspect, the surgical visualization and medical imaging device comprises an organic material selected from the group consisting of milk, tapioca, gelatin, pasta, and semolina flour.

In a sixth aspect, the surgical visualization and medical imaging device comprises a surgical vaginal manipulator comprising a cylindrical form having an end and a core, the surgical vaginal manipulator comprising a plastic containing indocyanine green dye in proportions suitable for near infrared fluorescence of the surgical vaginal manipulator when exposed to near infrared radiation.

In a seventh aspect, the surgical visualization and medical imaging device comprises a surgical uterine manipulator comprising a cup, a shaft operatively coupled to the cup, a guide ridge circumscribing the circumference of the cup, and an inflatable balloon within the cup, the surgical uterine manipulator comprising a plastic containing indocyanine green dye in proportions suitable for near infrared fluorescence of the surgical uterine manipulator when exposed to near infrared radiation.

In an eighth aspect, the present invention may be a system for robotically assisted surgical imaging comprising a first camera and a second camera; a white light source for illuminating a surgical field that is being imaged by the first camera and the second camera; a near infrared light source for providing a source of near infrared radiation to a surgical device comprising indocyanine green dye and a plastic; a computer having a processor, memory and access to computer readable media; the computer configured to receive brightness values for each coordinate on a coordinate map of a surgical field of view and output relative tissue depth and density.

In a ninth aspect, the present invention may include a computer program stored on computer readable media where the computer program executes the steps of: creating a coordinate map of a surgical field of view; assigning a coordinate to each location on the coordinate map; receiving brightness values for each coordinate; assigning relative tissue depth values for each coordinate based on the received brightness values; assigning tissue density values for each coordinate based on the received brightness values; creating a virtual image of the surgical field of view using the relative tissue depth values for each coordinate and the tissue density values for each coordinate; adding an image of the surgical field of view to the virtual image of the surgical field of view; and displaying the image of the surgical field of view with the virtual image of the surgical field of view on a computer monitor.

In a tenth aspect, the computer executed steps of assigning relative tissue depth and tissue density provide identification of tissue anomalies and masses.

In an eleventh aspect, the system further comprises a robotic arm. In a twelfth aspect, the near infrared light source has an intensity adjustment.

In a thirteenth aspect, the near infrared light source has an angle of incidence adjustment.

In a fourteenth aspect, the near infrared light source has a duty cycle adjustment.

In a fifteenth aspect, the present invention may be a computer based method for enhanced surgical imaging, the method comprising the steps of: creating a coordinate map of a surgical field of view on a computer having a processor, memory and computer readable media and storing said coordinate map on the computer readable media; assigning on the computer a coordinate to each location on the coordinate map; receiving on the computer brightness values for each coordinate from a digital imaging system configured to receive images of the surgical field of view when irradiated with a near infrared source; assigning on the computer relative tissue depth values for each coordinate based on the received brightness values; assigning on the computer tissue density values for each coordinate based on the received brightness values; creating on the computer a virtual image of the surgical field of view using the relative tissue depth values for each coordinate and the tissue density values for each coordinate; adding on the computer an image of the surgical field of view to the virtual image of the surgical field of view; and displaying on the computer the image of the surgical field of view with the virtual image of the surgical field of view on a computer monitor.

In a sixteenth aspect, the present invention may be a surgical visualization and medical imaging device comprising: a device comprising a plastic containing indocyanine green dye in proportions suitable for near infrared fluorescence of the device when exposed to near infrared radiation.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification and the attached drawings. As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

What is claimed is:

1. A medical device, comprising:
    a body having a predetermined volume that is formed from and filled throughout by a polymer, an amount of a fluorescence enhancer embedded in the polymer, and an amount of near infrared fluorescent dye embedded in the polymer;
    wherein the predetermined volume of the body, the amount of fluorescent enhancer, and the amount of near infrared fluorescence dye will respond to excitation energy from a near infrared energy source such that the body will emit near infrared fluorescence at a level sufficient to distinguish between any layers of human tissue adjacent to the body; and
    wherein the body forms at least a portion of a surgical manipulator selected from the group consisting of a vaginal manipulator, a bowel sizer, and a uterine manipulator.

2. The medical device of claim 1, wherein the level of near infrared fluorescence will pass through any layers of human tissue up to a depth of ten millimeters.

3. The medical device of claim 1, wherein the amount of near infrared fluorescent dye embedded in the polymer will produce near infrared fluorescence equivalent to the amount of near infrared fluorescence that is produced by indocyanine dye in ethanol at a concentration of four parts per million.

4. The device of claim 1, wherein the body is the head of the bowel sizer.

5. The device of claim 1, wherein the body is a vaginal manipulator.

6. The device of claim 1, wherein the body is a cup of the uterine manipulator.

7. The device of claim 6, wherein the cup includes a guide ridge.

8. The device of claim 1, wherein the near infrared fluorescent dye is indocyanine green.

9. The device of claim 1, wherein the polymer is selected from the group consisting of polycaprolactone, acrylonitrile butadiene styrene, polytetrafluoroethylene, and polycarbonate.

10. The device of claim 1, wherein the enhancer comprises milk powder.

11. A method of visualizing tissue during a surgical procedure, comprising the steps of positioning the device of claim 1 under the tissue to be visualized, exciting the device with a first frequency of near infrared radiation, detecting a second frequency of near infrared radiation emitted by the device, and displaying the second frequency of near infrared radiation emitted by the device for viewing.

12. The method of claim 11, wherein the second frequency of near infrared radiation emitted by the device penetrates the tissue to a depth of about ten millimeters.

13. The method of claim 12, wherein the step of displaying the second frequency of near infrared radiation emitted by the device for viewing comprises displaying the second frequency of near infrared radiation in combination with the visual spectrum.

14. The method of claim 13, wherein the step of exciting the device with a first frequency of near infrared radiation includes modulation of at least one of an intensity, an angle of incidence, and a duty cycle of a source of near infrared radiation.

15. The medical device of claim 1, wherein the amount of near infrared dye embedded in the polymer has a concentration of 50 parts per million.

16. The medical device of claim 15, wherein the fluorescence enhancer embedded in the polymer is an inorganic compound.

* * * * *